United States Patent [19]

Levesque

[11] 4,215,692
[45] Aug. 5, 1980

[54] ABSORBENT STRUCTURE

[75] Inventor: Yvon G. Levesque, Montreal, Canada

[73] Assignee: Johnson & Johnson, New Brunswick, N.J.

[21] Appl. No.: 7,280

[22] Filed: Jan. 30, 1979

Related U.S. Application Data

[63] Continuation-in-part of Ser. No. 879,832, Feb. 21, 1978, abandoned.

[51] Int. Cl.² ............................................. A61F 13/16
[52] U.S. Cl. ..................................... 128/287; 162/92
[58] Field of Search ........... 128/284, 285, 287, 290 R, 128/296, 156; 162/92, 141, 142; 428/243, 281, 287, 326

[56] References Cited

U.S. PATENT DOCUMENTS

| 610,957 | 9/1898 | Zschorner | 162/92 |
| 642,387 | 1/1900 | Tempied et al. | 128/156 |
| 1,328,267 | 1/1920 | Cowan | 162/92 |
| 4,047,531 | 9/1977 | Karami | 128/287 |

Primary Examiner—Robert W. Michell
Assistant Examiner—C. F. Rosenbaum
Attorney, Agent, or Firm—Jason Lipow

[57] ABSTRACT

An absorbent structure is provided comprising peat moss in combination with mechanical wood pulp, said wood pulp having a Canadian Standard Freeness of from about 30–600 and present in the ratios, by weight of wood pulp to peat moss, of greater than about 0.35. The absorbent structure, which may also contain other absorbent materials such as long-fibered chemical wood pulp, rayon or the like, exhibits improved absorbent properties in both liquid-holding capacity and liquid-retention capacity and maintains its structural integrity.

12 Claims, 7 Drawing Figures

U.S. Patent  Aug. 5, 1980  Sheet 1 of 3  4,215,692
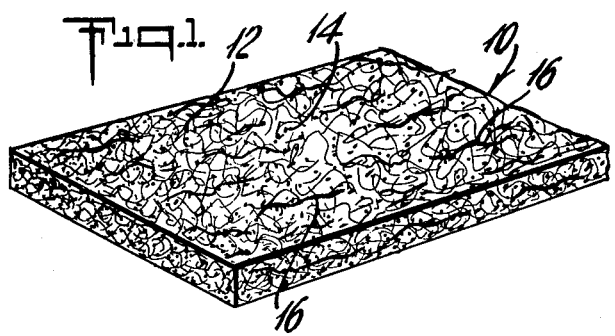
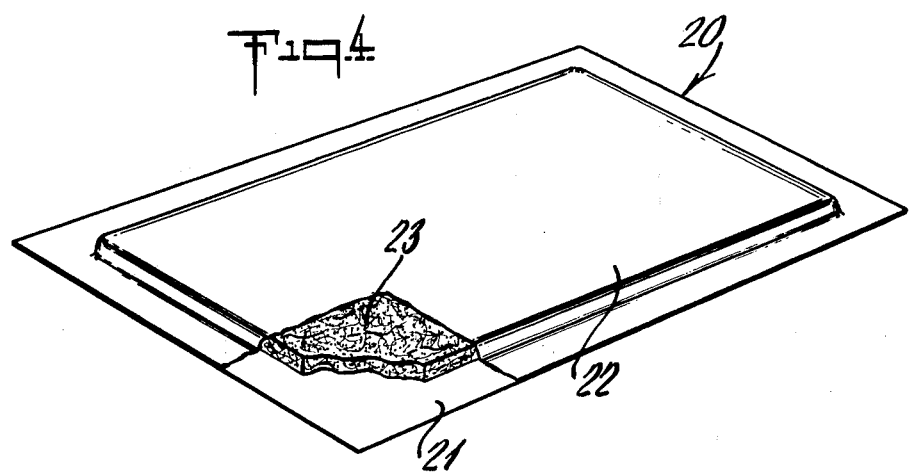
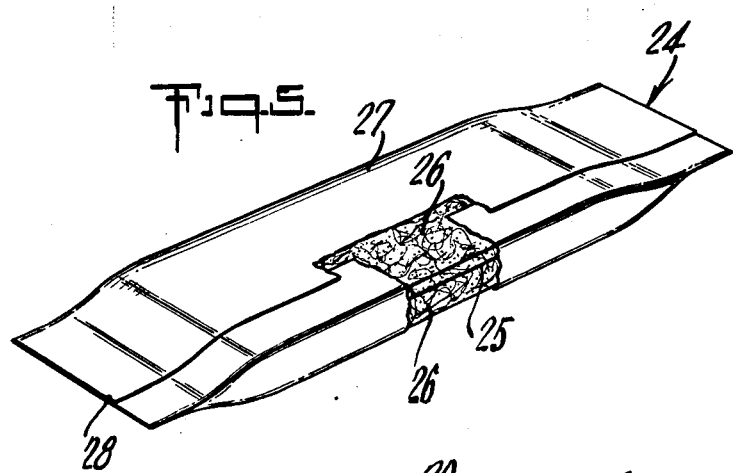
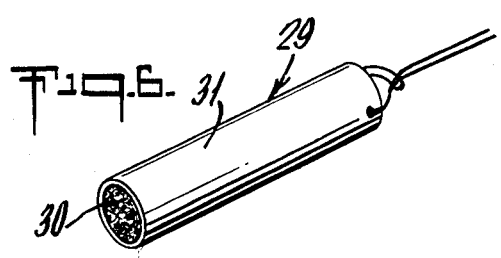

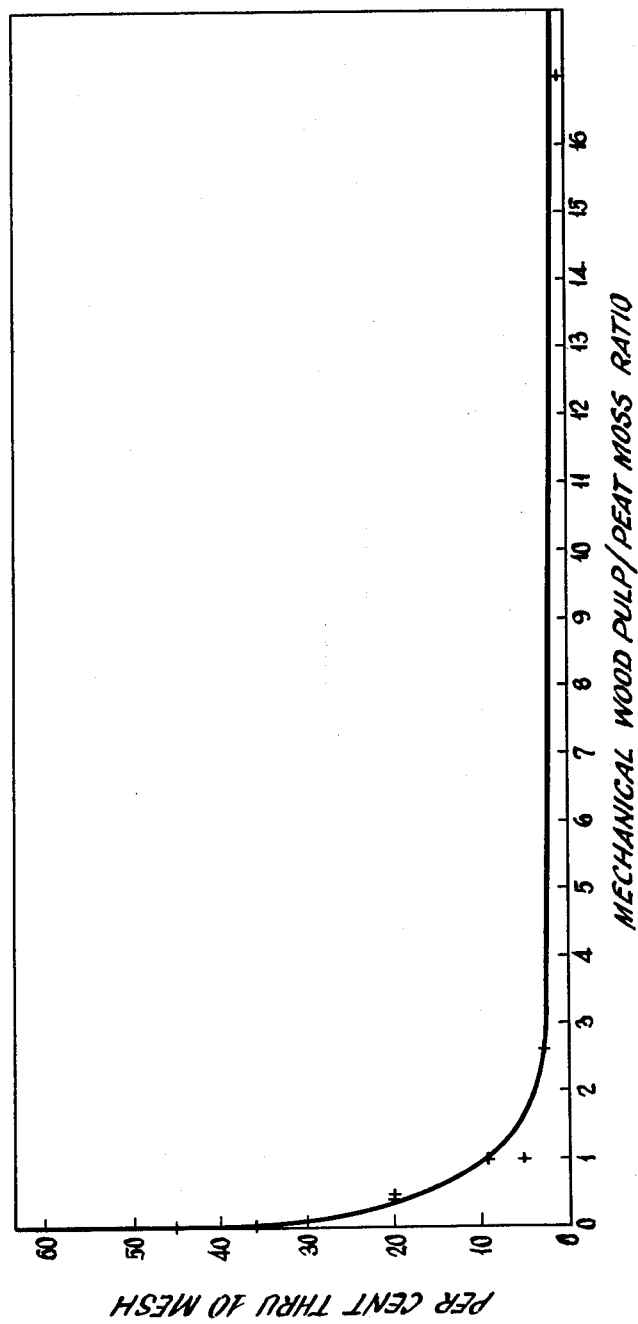

ABSORBENT STRUCTURE

This application is a continuation-in-part of Ser. No. 879,832, filed on Feb. 21, 1978 and now abandoned.

TECHNICAL FIELD

The present invention relates to absorbent products and more particularly to an improved absorbent structure for use in diapers, sanitary napkins and the like.

BACKGROUND OF THE ART

Many disposable products such as diapers, sanitary napkins, some tampons and some absorbent dressings contain a layer or core of highly absorbent material which is wrapped or contained by other relatively less absorbent materials. In some instances, such as in a diaper, the absorbent layer may be contained, at least on one of its surfaces, by an impervious film material. For example, a diaper may comprise a pervious upper layer, a highly absorptive center layer, and an impervious bottom layer. A sanitary napkin usually comprises a highly absorptive layer wrapped in a pervious layer. The absorptive layers used in disposable products usually comprise a plurality of layers of creped paper tissue or, in some instances, chemical wood pulp fibers in a fluffed or a loose, lightly compacted configuration.

For many years peat moss has been known as possessing good water-absorbing characteristics but, to date, has not been successfully incorporated as a primary ingredient in a structure suitable for use in diapers, sanitary napkins or dressings. It is believed the reason for this may be the intrinsic, extremely dark color of peat moss, the inability to handle peat moss and place it in a suitable configuration for wrapping, or perhaps a combination of these undesirable characteristics.

SUMMARY OF THE INVENTION

What I have discovered is a new and improved absorbent structure or core product. My new product, while being somewhat darker in color than fluffed, chemical wood pulp, is of sufficient lightness to have its off-color hidden by an outer wrappper. My new product may be handled and utilized as an absorbent core in diapers, napkins, absorbent dressings and the like. By incorporating the teachings of this invention, I have found that, unexpectedly, my new product exhibits improved liquid-retentive properties and is capable of maintaining its structural integrity.

The new product comprises bleached peat moss, in combination with finely divided mechanical wood pulp having a Canadian Standard Freeness of from about 30 to 600 and present in ratios, by weight of said wood pulp to peat moss of greater than about 0.35. The term "mechanical wood pulp" is meant to encompass those wood pulps which have been reduced to a finely divided state from the trunk and branches of trees after removal of bark and dirt but without any prior chemical treatment. Included in such materials are the groundwood pulps, refiner pulps and thermo mechanical pulps.

The bleached peat moss has a whiteness of at least about 70, as measured on the Hunter Luminus Reflective Scale, and maintains its raw peat porous structure, i.e., there is still a portion of the humic acids and lignin-like constituents remaining in the bleached peat moss to maintain its open, porous, leaf-like structure. This open structure is believed to be the major factor in producing the highly desirable, absorbent properties exhibited by this peat moss. Unfortunately peat moss in this open, porous condition is quite brittle and does not, by itself, withstand the kind of handling absorbent products such as diapers, napkins, tampons and the like are subject to. Still further, the particles of peat moss are not self-entangling, such as are long-fibered absorbent material, or self-adherent. In short, the peat moss, per se, has been found to be difficult to handle and incapable of being formed into a self-sustaining form having any structural integrity.

It has now been discovered that those shortcomings of the peat moss described herein can be overcome and that an absorbent structure having both surprisingly good absorbent properties as well as structural integrity can be provided by including, in admixture with the peat moss, relatively fine mechanical wood pulp having a Canadian Standard Freeness (hereinafter, CSF) of from about 30–600. Such wood pulp, which may be selected from pulps such as groundwood pulp, refiner wood pulp and/or thermomechanical wood pulp, generally have shorter fiber lengths than the chemical pulps, e.g., the sulfite or sulfate pulps usually associated with diapers, napkins and tampon products. The fine mechanical wood pulps are generally characterized by their drainage and compacting characteristics which are measured by "freeness"; i.e., Canadian Standard Freeness as measured by TAPPI Test Method T-227. It has been discovered that the structural integrity of pulp fluff that has been made by grinding board formed from an aqueous slurry of a mixture of peat moss and the herein prescribed finely divided mechanical wood pulp is extremely sensitive to the ratio by weight, of the wood pulp to the peat moss. Specifically, the mixture loses essentially all its cohesiveness at such ratios below 0.35. Preferably such ratio should be maintained above 0.38.

The mixture of peat moss and mechanical wood pulp may be supplemented with other absorbent materials such as the more commonly used long-fibered wood pulps such as sulfite or sulfate pulp or rayon fibers or mixtures of these. In forming products from the absorbent structure of this invention, a core of the prescribed material may be wrapped about its entire periphery with a pervious layer such as a non-woven fabric, as for example in a sanitary napkin. Alternatively, the core may be interspersed between a pervious layer such as a non-woven fabric and an impervious layer such as thermoplastic film, as in a disposable diaper.

BRIEF DESCRIPTION OF THE DRAWINGS

The present invention will be more fully described when taken in conjunction with the accompanying drawings wherein:

FIG. 1 is a perspective view of a new, improved absorbent product of the present invention.

FIG. 4 is a perspective view, with a portion cut away, of a disposable diaper incorporating the absorbent product of the present invention;

FIG. 5 is a perspective view, with a portion cut away, of a sanitary napkin incorporating the absorbent product of the present invention;

FIG. 6 is a perspective view of a tampon, with a portion cut away, which incorporated the absorbent product of the present invention; and FIG. 7 is a graphical presentation of data showing the relationship of the ratio, by weight of mechanical wood pulp to peat moss, to the structural integrity of the resulting structure.

DETAILED DESCRIPTION OF THE DRAWINGS

Figure 2:
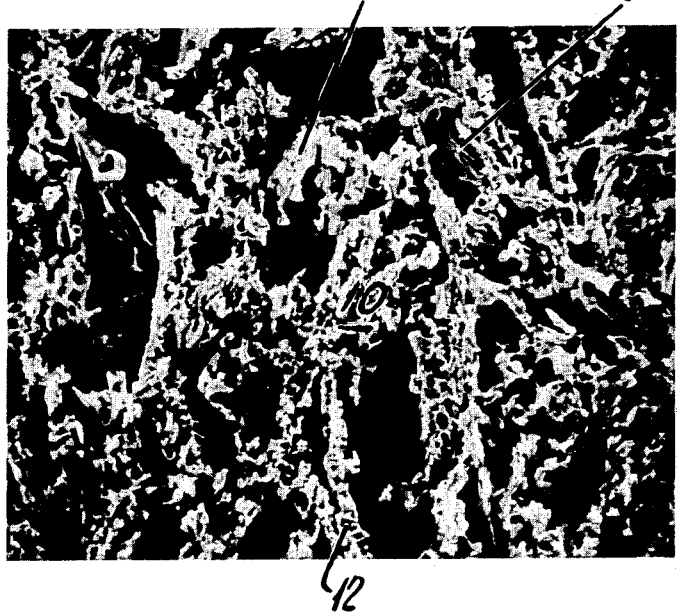
FIG. 2 is a photomicrograph at an original enlargement of 160 times of a new and improved absorbent product of the present invention.

FIGS. 1 and 2 show the new and improved absorbent product or core 10 of the present invention. This core 10 comprises bleached peat moss 12 having a whiteness of at least about 70, as measured on the Hunter Luminus Reflective Scale, combined with finely-ground mechanical wood pulp 14 having a Canadian Standard Freeness of from about 30–600 and present in the ratios, by weight of wood pulp to peat moss, of at least about 0.35. Preferably, this ratio is at least about 0.4 and still more preferably at least about 0.5 Also included in the core 10 are other absorbent materials such as long-fibered chemical wood pulp 16 and long-fibered rayon.

Figure 3:
FIG. 3 is a photomicrograph at an original englargement of 160 times of the bleached peat moss used in the absorbent products of the present invention.

The peat moss 12, as can be seen more closely in the photomicrograph of FIG. 3, has a leaf-like structure with open pores 18 and maintains this structure in the absorbent core 10. The bleached peat moss 12 has a degree of whiteness of at least about 70, when measured on the Hunter Color and Color Difference Scale, as set forth by ASTM D-2244 Color Scale System "C" method.

I prefer to start with peat moss (sphagnum) which will hold at least 15 and preferably 20 times its weight of water. I screen the peat moss between 10 and 100 mesh screens. The material that stays on a 10 mesh screen, primarily roots and branches, is discarded. The material that passes through a 100 mesh screen; namely, fines, which add little to absorbency and are difficult to bleach, is also discarded. Hence, my starting peat moss is from about 0.15 mm. (100 mesh) to 1.8 mm. (10 mesh).

The peat moss is bleached by treatment with both chlorine and calcium in the form of lime stone. The bleaching may be carried out as a batch operation; that is, where the peat moss is diluted with water to a concentration of about 2% by weight, treated with chlorine, followed by a calcium carbonate treatment, followed by acid washes and water washes to provide the desired degree of whiteness. A specific and preferred method of bleaching is described in our co-pending application Ser. No. 879,833, filed on Feb. 21, 1978, and incorporated herein by reference.

The bleached peat moss is dried to a degree where it can be handled and may actually be formed into a board or sheet-type layer if desired. When formed into a board, it is preferred that it be formed along with the finely-ground mechanical wood pulp 14 and optimally the long-fibered wood pulp 16, and then this admixture further dried together into the finished board. In producing the absorbent core, the peat moss and mechanical wood pulp are ground by standard wood pulp grinding operations, such as a hammer mill, and laid down on a carrier sheet, which may be the wrapping sheet or a piece of tissue, in the desired amounts as is well known in the art.

The finely-ground mechanical wood pulp may be selected from the group consisting of groundwood pulp, thermomechanical pulp and refiner wood pulp. Groundwood pulp is essentially trees and branches which have been debarked, cleaned and then ground into particle matter. Refiner wood pulp differs from groundwood pulp only in that the grinding step utilizes a refiner, i.e., a disk-like device well known in the art and generally having metalic ribs at the peripheral sections thereof which last contact the wood particles and help to separate the wood fibers without excessively damaging them. Thermomechanical wood pulp is similar to refiner pulp with the exception that the wood particles are heated when in the refiners, usually with steam, and this heating further aids in separating the wood fibers. The common characteristic of these mechanical pulps is that no attempt has been made to separate the fibers by chemical means although they may later, after being reduced to fine particulate matter, be subjected to chemical treatment, e.g., bleaching.

These mechanical pulps are commonly characterized by the term "freeness," which is measured by the Canadian Standard Freeness Test (TAPPI Test Method T-227). This test essentially measures the rate of drainage of pulp and, in effect, the degree of compactness. The preferred Canadian Standard Freeness value for the mechanical wood pulp materials incorporated in the absorbent cores of this invention should vary between about 30–600 and preferably from about 60–600.

The long-fibered wood pulp may comprise approximately 5–20% by weight of the total weight of the core and may be chosen from such chemically treated or formed wood pulp as sulphite and sulphate wood pulp. It is preferred that the wood pulp selected be chosen from soft wood materials, although hard wood fibers may also be used. The term "long-fibered wood pulp" is meant to describe pulps having at least 40% by weight, made up of fibers of a length of 1/16" or more, and preferably, about 50% by weight of the wood pulp consisting of fibers of at least 1/16" in length.

In figure 4, there is shown a disposable diaper 20 which incorporates the new and improved absorbent core of the present invention. The diaper comprises a backing 21 which may be a thermoplastic, fluid impervious, film material. The diaper also comprises a facing 22 layer which is a material pervious to fluids and may be a nonwoven fabric of any of the standard types such as the spunbond products, the spunlaced products, standard carded non-woven fabrics, or in some instances, even pervious film materials may be used. Disposed between the facing layer and backing layer, and slightly smaller than the layers, is the new and improved absorbent core 23 of the present invention.

In FIG. 5, there is shown a sanitary napkin 24 which incorporates the absorbent core of the present invention. In this construction the napkin may comprise a center barrier sheet 25 which may be a thermoplastic film. On each side of this center sheet is an absorbent core product which in this instance is the absorbent core 26 of the present invention. The three-piece laminate is wrapped about its entire periphery with a suitable pervious material 27 such as the standard non-woven fabrics. The wrapping extends beyond the ends of the absorbent core product to form tabs 28 for attaching the napkin.

In FIG. 6 there is shown a tampon 29 which incorporates in its center the absorbent core product 30 of the present invention. The absorbent core is wrapped about its entire periphery with suitable pervious wrapping material 31 such as the standard non-woven fabrics.

The invention will be further described in conjunction with the following examples. In each of these examples the absorbent has been treated so as to include a wetting agent in quantities of less than 0.5% by weight of dry absorbent. The wetting agent used is a sodium dioctyl sulfo succinate containing agent manufactured by the Rohm & Haas Company and sold by them under the tradename Triton GR-5.

EXAMPLE 1

Approximately 28 pounds of raw peat moss is classified using a Sweco classifier. The wet classification removes the fines, that is, materials less than 100 mesh or smaller than 150 microns in diameter. The classification also removes the large pieces of material; that is, materials larger than 10 mesh, which are the roots, etc. The 10 to 100 mesh fraction is bleached by reaction with 21 pounds of calcium carbonate and 18.9 pounds of chlorine. The bleached peat is dewatered to remove liquid from a 1% solids dispersion to a 5% solids dispersion. The peat is washed with tap water back to a consistency of 1% solids and dewatered again to 5% solids. The peat is placed in a tank and brought to 1% consistency with water and 10 pounds of 22 Baume' hydrochloric acid. The resultant bleached peat moss has a whiteness of about 72 on the Hunter scale as previously described.

The 1% bleached peat moss is held in a tank. About 26¼ pounds of groundwood pulp and 5¼ pounds of bleached Kraft woodpulp are dispersed in water to a 2% solids consistency. This wood pulp mixture and the acidified bleached peat are mixed together to form a misture of 0.7% solids consistency and containing 21 pounds bleached peat, 26¼ pounds groundwood pulp and 5¼ pounds of long-fibered wood pulp. The mixture is beaten with a minor amount of agitation or shear so as not to abrade the peat moss leaf, and the mixture flowed onto a Fourdrinier wire with vacuum to dewater the mixture and form a board. The board is forced air dried at about 350° F. and rolled up. The board is ground by conventional equipment in a Hammer mill to produce a fluffed, absorbent core product.

As previously mentioned, the resultant improved absorbent product has improved capillarity compared to chemical wood pulps or groundwood pulps per se. Furthermore, our new product has improved liquid retention properties, that is, holding of absorbed liquids under increased pressure, than either the groundwood pulps or the chemically formed wood pulps when used alone.

EXAMPLE 2

A plurality of absorbent core products are made by mixing and grinding together various combinations of chemical, long fibered, wood pulps; groundwood pulp; unbleached peat moss; and bleached peat moss. The absorbent core products are formed and measured for Liquid Uptake, Liquid Retention After Saturation, and Liquid Retention Under Pressure as described in the following test methods.

Liquid Uptake Test Method

A 7.7 cm. diameter piece of the absorbent core to be tested is placed on top of a fritted glass filter plate and pressed with a confining pressure of 2.5 grams/per $cm.^2$. The underside of the fritted glass plate is in contact with liquid in the form of a column of liquid extending 40 centimeters below the porous plate. The column of liquid is in a calibrated burette and the volume amount absorbed is measured after a five-minute period, and a one-day period (reaching essentially equilibrium). The column is moved upwards to within 7½ centimeters below the porous plate and allowed to come to equilibrium and the volume amount absorbed measured. The column is moved to within 1 centimeter of the porous plate and again allowed to come to equilibrium and the volume amount absorbed measured.

Liquid Retention After Saturation Test Method

The same piece of absorbent core used in the Liquid Uptake Test is fully saturated and the column moved back to 1 centimeter below the core level and a volume measurement taken, and then moved back to 40 centimeters below the core level and a volume measurement taken. This test determines the amount of liquid retained after saturation.

Liquid Retention Under Pressure Test Method

Using another apparatus, a piece of absorbent core is placed on top of perforated steel plate and fully saturated with liquid. The volume amount of saturation is measured with no pressure on top of the absorbent core, with a pressure of 20 grams per square centimeter on top of the core, and with a pressure of 105 grams per square centimeter on top of the absorbent core.

As previously mentioned, a number of cores having the composition as shown across the top of the following table I were measured for various absorptive properties as shown along the lefthand side of the table.

TABLE I

| SAMPLE: | | | 1 | 2 | 3 | 4 | 5 | 6 | 7 |
|---|---|---|---|---|---|---|---|---|---|
| COMPOSITION | | | | | | | | | |
| COMPONENT | | | PERCENT BY WEIGHT | | | | | | |
| LONG FIBER WOOD PULP | | | 10 | 10 | 10 | 10 | 10 | 10 | 10 |
| BLEACHED PEAT MOSS | | | — | 5 | 25 | 45 | 65 | 90 | — |
| RAW PEAT MOSS | | | — | — | — | — | — | — | 90 |
| GROUNDWOOD PULP | | | 90 | 85 | 65 | 45 | 25 | — | — |
| ABSORBENT PROPERTIES | | | | | | | | | |
| TEST | DURATION | PRESSURE | LIQUID HELD (grams liquid/100 grams of dry sample) | | | | | | |
| LIQUID | 5 mins. | −40 cm.liq. | 120 | 140 | 160 | 190 | 230 | 250 | 100 |
| UPTAKE | equilibrium | −40 cm.liq. | 270 | 300 | 350 | 400 | 440 | 550 | 455 |
| | " | 7.5 cm.liq. | 660 | 705 | 780 | 820 | 800 | 955 | 945 |
| | " | 1.0 cm liq. | 1,540 | 1,470 | 1,660 | 1,590 | 1,490 | 1,660 | 1,950 |
| RETENTION | equilibrium | − 1 cm liq. | 1,625 | 1,690 | 1,760 | 1,775 | 1,610 | 1,825 | 2,115 |
| AFTER | " | −40 cm.liq. | 380 | 420 | 485 | 545 | 550 | 690 | 640 |
| SATURATION | | | | | | | | | |
| RETENTION | " | 0 $g/cm^2$ | 2,075 | 2,100 | 2,090 | 2,080 | 2,060 | 1,955 | 2,440 |
| UNDER | " | 20 $g/cm^2$ | 1,465 | 1,440 | 1,640 | 1,530 | 1,550 | 1,530 | 1,875 |

TABLE I-continued

| PRESSURE | " | 105 g/cm² | 715 | 770 | 810 | 845 | 865 | 920 | 1,000 |

EXAMPLE 3

A series of fluff material is prepared by grinding, into fluff, board formed from slurries of mixtures of peat moss, mechanical pulp (groundwood) and chemical pulp. The composition of each of the samples is shown in Table II below. The samples are tested for their structural integrity by placing a 5 gram sample in the pan of a RoTap Testing Sieve Shaker equipped with a 10 mesh Tyler screen. This apparatus is manufactured by W. F. Tyler Inc., a subsidiary of Combustion Engineering Inc. of Ohio, U.S.A. The pan of the RoTap Shaker, which measures 8 inches in diameter, is filled to a depth of 2 inches. The RoTap Sieve Shaker is operated for 25 cycles, and the quantity of material passing through the Tyler screen during operation is collected, weighed and reported, on a weight percent based on the original 5 gram sample, as Losses in Table II below. FIG. 7 is a graphical representation of the data in Table II, showing the relationship between the ratio, by weight of the finely-ground wood pulp to the peat moss, and the structural integrity of the resulting structure as manifested by percent Loss through the screen.

TABLE II

| SAMPLE: Composition (%) | 1 | 2 | 3 | 4 | 5 | 6 | 7 | 8 | 9 | 10 |
|---|---|---|---|---|---|---|---|---|---|---|
| Peat Moss | 100 | 90 | 90 | 70 | 65 | 45 | 50 | 65 | 5 | 0 |
| Groundwood pulp | 0 | 0 | 0 | 30 | 25 | 45 | 50 | 25 | 85 | 90 |
| Long Fibered Wood Pulp | 0 | 10 | 10 | 0 | 10 | 10 | 0 | 10 | 10 | 10 |
| Ratio* | 0 | 0 | 0 | 0.428 | 0.385 | 1.0 | 1.0 | 2.6 | 17.0 | |
| Losses (%) | 100 | 36 | 45 | 20 | 20 | 9.4 | 5.0 | 2.6 | 1.6 | <1 |

*Weight of groundwood pulp/weight of peat moss

As Table II and FIG. 7 illustrate, the losses and, hence, the structural integrity of the fluff is greatly dependant upon the ratio of mechanical wood pulp to peat moss. At ratios of essentially zero, extremely large losses result varying from about 40-100%. Such losses would be intolerable in absorbent products such as diapers, napkins and tampons. If material exhibiting such losses were incorporated in such products, a great quantity of the peat moss would separate from the remainder of the absorbent material and dust out of the product. Additionally, the off-color of the peat moss would become evident to the user. The separated peat moss would be further broken down owing to its brittleness and would lose its effectiveness as an absorbent material. Tolerable losses are encountered only when the ratios of mechanical wood pulp approach the value of about 0.35 and preferably around 0.4. At the very high ratios, it can be seen that the losses are reduced to negligible levels.

What is claimed is:

1. An absorbent product comprising peat moss and mechanical wood pulp, said wood pulp having a Canadian Standard Freeness of from about 30-600, and present in a ratio, by weight of said mechanical wood pulp to said peat moss, of more than about 0.35; said peat moss having a color intensity of at least 70 on the Hunter Color Scale System "C".

2. The absorbent product of claim 1 wherein said mechanical wood pulp is present in a ratio, by weight of said mechanical wood pulp to peat moss, of more than about 0.38.

3. The absorbent product of claim 1 wherein said mechanical wood pulp is refiner wood pulp.

4. The absorbent product of claim 1 wherein said mechanical wood pulp is thermomechanical wood pulp.

5. The absorbent product of claim 1 further comprising long-fibered absorbent material.

6. The absorbent product of claim 5 wherein said long-fibered material is chemical wood pulp.

7. The absorbent product of claim 5 wherein said long-fibered absorbent material is rayon.

8. The absorbent product of claim 1 wherein said peat moss has a particle size distribution range of from 10-100 mesh.

9. The absorbent product of claim 1 wherein said finely-ground wood pulp has a Canadian Standard Freeness of from about 60-300.

10. A disposable diaper comprising an impervious backing sheet, a pervious facing sheet and an absorbent core smaller than said sheets and disposed therebetween, said absorbent core comprising peat moss and mechanical wood pulp, said wood pulp having a Canadian Standard Freeness of from about 30-600 and present in a ratio, by weight of said mechanical wood pulp to said peat moss, of more than about 0.35.

11. A sanitary napkin comprising an absorbent core having a cover enveloping said core, said absorbent core comprising peat moss and mechanical wood pulp, said mechanical wood pulp having a Canadian Standard Freeness of from about 30-600 and present in a ratio, by weight of said wood pulp to said peat moss, of more than about 0.35.

12. A catamenial tampon comprising an absorbent core and a fluid-pervious cover enveloping said core, said absorbent core comprising peat moss and mechanical wood pulp, said wood pulp having a Canadian Standard Freeness of from about 30-600 and present in a ratio, by weight of said wood pulp to said peat moss, of more than about 0.35.

* * * * *